(12) United States Patent
Nellenbach et al.

(10) Patent No.: US 8,822,375 B2
(45) Date of Patent: Sep. 2, 2014

(54) METHOD FOR ACTIVATING COLORANT ASSOCIATED WITH AN ARTICLE

(75) Inventors: Eva Grace Nellenbach, Reading, OH (US); Robert Clark Avery, Jr., Mason, OH (US)

(73) Assignee: The Procter & Gamble Company, Cincinnati, OH (US)

(*) Notice: Subject to any disclaimer, the term of this patent is extended or adjusted under 35 U.S.C. 154(b) by 77 days.

(21) Appl. No.: 13/528,338

(22) Filed: Jun. 20, 2012

(65) Prior Publication Data

US 2012/0329647 A1    Dec. 27, 2012

Related U.S. Application Data

(60) Provisional application No. 61/500,820, filed on Jun. 24, 2011.

(51) Int. Cl.
*B41M 5/28* (2006.01)
*G03F 1/00* (2012.01)

(52) U.S. Cl.
CPC ............... *B41M 5/285* (2013.01); *G03F 1/00* (2013.01); *B41M 2205/14* (2013.01)
USPC ............................................. 503/201; 430/5

(58) Field of Classification Search
CPC ....... B41M 5/285; B41M 2205/14; G03F 1/00
USPC ....................................... 503/200–226; 430/5
See application file for complete search history.

(56) References Cited

U.S. PATENT DOCUMENTS

| 6,461,775 B1 * | 10/2002 | Pokorny et al. ............... 430/7 |
| 8,083,973 B2 | 12/2011 | Jarvis |
| 2009/0075816 A1 | 3/2009 | Kawahara et al. |
| 2011/0104459 A1 | 5/2011 | Arora et al. |

FOREIGN PATENT DOCUMENTS

| JP | 05105779 | 4/1993 |
| JP | 2001/018239 | 1/2001 |
| WO | WO-02/06058 | 1/2002 |

OTHER PUBLICATIONS

PCT International Search Report, mailed Sep. 26, 2012, 6 pages.

* cited by examiner

*Primary Examiner* — Bruce H Hess
(74) *Attorney, Agent, or Firm* — Andrew J. Hagerty

(57) ABSTRACT

Methods and apparatuses for activating colorant in selected regions of an article in which the colorant is incorporated are described. The colorant activation can create various desired visual aspects.

16 Claims, 6 Drawing Sheets

METHOD FOR ACTIVATING COLORANT ASSOCIATED WITH AN ARTICLE

CROSS REFERENCE TO RELATED APPLICATIONS

This application claims the benefit of U.S. Provisional Application No. 61/500820, filed Jun. 24, 2011.

FIELD OF THE INVENTION

The present invention is generally directed to methods and apparatuses for activating colorant associated with an article.

BACKGROUND OF THE INVENTION

Colorants that can change colors when exposed to an external stimulus or energy source and their use in manufactured articles are known. Examples include thermochromic materials that can change color by a change of temperature, photoreactive materials that can change color through exposure to electromagnetic radiation, and piezochromic materials that can change color via pressure. The activatable colorants can be applied to an article's outer surface, such as by printing or spraying. With this incorporation approach, the ultimate design features brought to life by activating the colorant can be controlled with the methods used to apply the colorants to the article.

Activatable colorants can also be incorporated into the material from which an article is made. For example, plastic articles can be molded with a melt material that contains both a base polymer resin and an activatable colorant. The as-molded article will have an initial appearance which can then be altered through exposure to an energy source such as an ultraviolet lamp. Since the activatable colorant is essentially dispersed throughout the entire molded article, creating a definable design in the article by selectively activating portions of the colorant can present challenges. And articles that include nonplanar or other complex geometrical features can increase the difficulty of selectively activating only portions of an incorporated colorant due to the need to manipulate the relationship between the article and the stimulus employed to activate the colorant.

SUMMARY OF THE INVENTION

The present invention provides methods and apparatuses for activating colorant in selected regions of an article in which the colorants are incorporated to create desired visual aspects. The methods and apparatuses provided herein are not limited by the manner in which activatable colorants are incorporated into the article. That is, embodiments of the present invention can be employed for activating colorants that are part of the material from which an article is made, as well as colorants that are added to a manufactured article.

In some embodiments, a mask having an open area design defined therein is positioned between an energy source and the article. The article is then moved from a first position to a second position while energy is being directed through the mask and onto/into the article so that the activatable colorant is activated in a plurality of locations, whereby the open area design from the mask is imparted on/within the article. The mask may be held stationary while the article is moved and energy is being transmitted from an energy source.

In one embodiment, an article comprising an activatable colorant is provided. The article includes a first surface portion and a second surface portion that faces in a different direction than that of the first surface. A mask with an open area design is placed between the article and an energy source. Energy is directed through the mask open area and onto/into the first surface portion and then onto/into the second surface portion. The mask is held stationary while both of the energy transmissions are conducted.

In another embodiment, an article comprising an activatable colorant is provided. The article comprises a nonplanar portion. A mask with an open area design is placed between the article and an energy source. Energy is directed through the mask open area and onto/into the article so that the open area design is created on and/or within the nonplanar portion of the article.

In another embodiment, an energy source and an article comprising an activatable colorant are provided. A normal force is applied to the article so that a portion of the article that is perpendicular to the energy source is greater in area dimension that that in the absence of the applied normal force. Energy is directed onto/into the article to alter the visual appearance of the article.

In yet another embodiment, an electromagnetic radiation and an article comprising an activatable colorant are provided. Electromagnetic radiation is directed onto/into the article whereby a design is created on and/or within a first portion of the article through activation of at least some of the colorant. The article is subsequently heated so that at least one of the design and a second article portion changes color.

In another embodiment, an energy source and a tubular member are provided. The tubular member includes a closable end and an activatable colorant. Energy is directed from the energy source and onto/into the article whereby a design is created on/within a portion of the article. The closable end is then closed with application of heat and pressure.

The present invention is not limited to the particular embodiments described above. And features from one embodiment described herein can be combined with features from a second described embodiment to yield alternative embodiments.

BRIEF DESCRIPTION OF THE DRAWINGS

The following detailed description of specific embodiments of the present invention can be best understood when read in conjunction with the drawings enclosed herewith.

DETAILED DESCRIPTION OF THE INVENTION

Detailed Description

Figure 1:
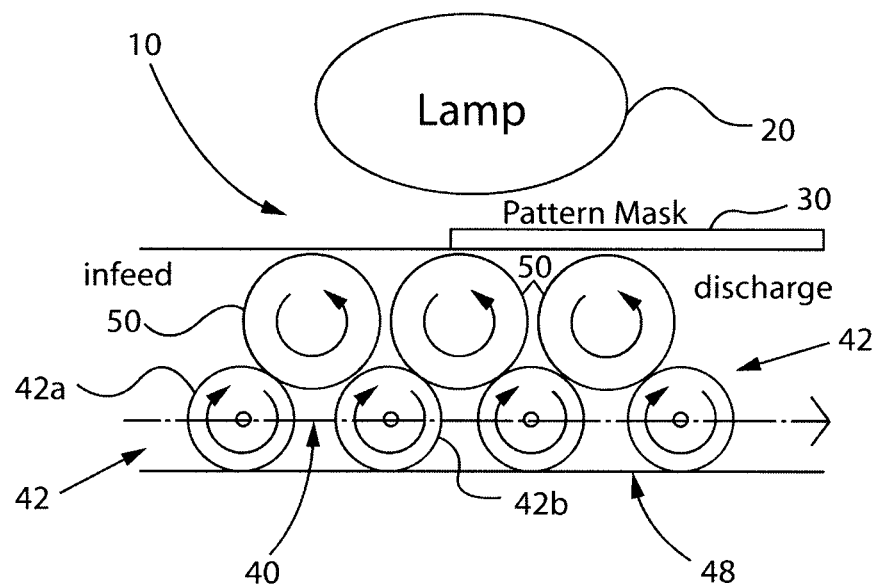
FIG. 1 is a first embodiment of a system for activating colorant associated with an article.

The following text sets forth a broad description of numerous different embodiments of the present invention. The description is to be construed as exemplary only and does not describe every possible embodiment since describing every possible embodiment would be impractical, if not impossible, and it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

It should also be understood that, unless a term is expressly defined in this specification using the sentence "As used herein, the term '_____' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such a claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Embodiments described herein generally relate to methods and apparatuses for activating colorants associated with articles. As used herein, the term "article" can include both complete manufactured products and manufactured components that are combined with other components prior to their use or sale to customers. The present invention is not limited to a particular type of article. The articles can be disposable, durable or semi-durable. The articles can be made from a variety of materials, including, for example, paper, plastic, and metal. The articles can comprise multiple material types, such as, for example, fibers, thermoplastic polymers, and thermoset polymers. Articles comprising more than one starting material may have activatable colorants associated with all of the starting materials or only some of the starting materials.

Plastic consumer products are one category of articles that can be acted on by the methods and apparatuses of the present invention. The plastic articles can be formed via extrusion, blow molding, and injection molding for example. A representative, non-limiting list of plastic articles includes feminine hygiene applicators (e.g., an applicator for a tampon, pessary or other intravaginal product), toothbrushes and toothbrush handles, razor handles, cleaning device handles, packaging components, dispensers, cosmetic devices, and electronic devices.

Colorants that can be activated with the methods and apparatuses of the present invention include those that can change color when exposed to energy from an external stimulus. Activatable colorants can include chemicals, monomers and polymers that are capable of being affected by an external stimulus. Examples include thermochromic materials that can change color by a change of temperature, photoreactive materials that can change color through exposure to electromagnetic radiation, and piezochromic materials that can change color via pressure. The color change associated with the activatable colorants can be irreversible, reversible, or quasi-reversible. Activatable colorants can either be coated onto articles or components thereof, such as on films or fibers, or can form an integral part of an article by being added, for example, to the raw materials from which they are made. Exemplary activatable colorants are described in greater detail below.

a) Thermochromic Materials

Thermochromic pigments are organic compounds that effectuate a reversible or irreversible color change when a specific temperature threshold is crossed. A thermochromic pigment may comprise three main components: (i) an electron donating coloring organic compound, (ii) an electron accepting compound and (iii) a solvent reaction medium determining the temperature for the coloring reaction to occur. One example of a commercially available, reversible thermochromic pigment is ChromaZone® Thermobatch Concentrates available from Thermographic Measurements Co. Ltd. Thermochromic pigments and the mechanism bringing about the temperature triggered color change are well-known in the art and are for example described in U.S. Pat. Nos. 4,826,550 and 5,197,958. Other examples of thermochromic pigments are described in U.S. Patent Application Publication No. 2008/0234644A1. Alternatively, the thermosensitive pigment may be of a microcapsule type which is known in the art of thermosensitive pigments.

b) Piezochromic Materials

Any piezochromic materials disclosed in the art are suitable herein as long as they meet the necessary health and safety requirements. An example is disclosed in U.S. Pat. No. 6,330,730. In one example the piezochromic material is thermochromic and responds to a temperature increase caused by applied pressure. In another example the piezochromic material comprises a dye, which is encapsulated into microcapsules. Upon application of pressure these capsules break and release the dye, which then becomes visible. The color intensity is directly linked to the amount of pressure applied. Typical piezochromic materials require a pressure of from 14 to 140 kPa. Most typical piezochromic color change materials can change their color in an irreversible fashion after exertion of pressure. This is due to the fact that the color change was achieved by the destruction of microcapsules, in which the substances for achieving the color change were encapsulated.

c) Photoreactive Materials

Photoreactive materials can change color in response to exposure to electromagnetic radiation. The color change can be irreversible providing a permanent change in color or it can be reversible providing a temporary change in color.

Photochromic materials are those that reversibly change color when exposed to light or changes in light intensity. Photochromic materials typically provide a reversible color change transitioning from a colorless state to a color state upon exposure to light and back to a colorless state when reversed. Exemplary photochromic materials are described in U.S. Pat. Nos. 6,306,409; 6,080,415; and 5,730,961.

Polychromic materials are those which are capable of generating multiple colors. Compounds based upon diacetylene, X—C≡C—C≡C—Y, when polymerized, are known to take on different color properties. Polymerization is typically achieved by exposure to certain types of radiation, such as ultraviolet radiation. Varying the intensity of the radiation causes differing degrees of polymerization, and different colors or shades of colors. Exemplary polychromic materials are disclosed in PCT publication nos. WO 2009/093028A2 and WO 2009/081385 A2. The disclosed compounds can undergo a color change upon irradiation, and have the general structure: X—C≡C—C≡C—Y—(CO)n-QZ wherein X is H, alkyl or —Y—(CO)n-QW; each Y is the same or a different divalent alkylene group; Q is O, S or NR; R is H or alkyl; W is H, alkyl or Z; each Z is the same or a different unsaturated alkyl group; and each n is 0 or 1. The type of radiation that performs the color change reaction with the diacetylene compounds includes laser or non-coherent, broadband or monochromatic radiation. Specific radiation types include ultraviolet, near, mid or far infrared, visible, microwave, gamma ray, x-ray or electron beam.

Another example of a photoreactive material is a thermoplastic material comprising polymer mixed with a charge transfer agent and a photo acid generating agent such as those described in U.S. Patent Application Publication No. 2009/0191476A1. Exposure of the thermoplastic material comprising the charge transfer agent and photo acid generating agent to irradiation can bring about a color change reaction which can be used to create text, artwork, devices or other images and effects. Another application describing photoreactive materials providing permanent color change includes PCT publication no. WO 2009/081385, which describes thermoplastic material comprising polychromic substance wherein the polychromic substance is a functionalized diacetylene having a formula which has a general structure that is described therein.

Activation of photoreactive materials can be achieved using an ultraviolet lamp. One example is the Coil Clean (CC) Series ultraviolet fixtures available from American Ultraviolet (Lebanon, Ind.). Another UVC exposure unit suitable for use in activation of photoreactive materials consists of a metal enclosure containing 8 UV amalgam lamps and 8 ballasts with individual circuits for individual lamp controls and a fan for cooling lamps to maintain temperature. The lamps are 357 mm in length and are available from American Ultraviolet as part number GML750A. Other examples of equipment that may be used for activation of photoreactive materials include the J3825 MonoCure Lamphead from Nordson UV Limited (Berkshire UK) and the 270S UV Lamp Assembly and Power Supply by Integrated Technology. The type of lamp within the unit may be changed to vary the spectral output as needed. Exemplary bulb types include "H", "V", "D" and "Q". Medium pressure Hg ultraviolet lamps are suitable for use in the methods of the present invention. DROPCURE lamp systems from Baldwin Technology Company include medium pressure Hg ultraviolet lamps. DROPCURE lamp systems can be configured to provide up to 600 W/in. and are water cooled to eliminate the need for high airflow and exhaust to maintain targeted temperatures of both the lamp and the materials/equipment being exposed to the ultraviolet energy. In one embodiment, the activation system is capable of activating colorant associated with articles translated at a rate of about 25 meters per minute. In another embodiment, the activation system is capable of activating colorant with an energy exposure dwell time of about 7 milliseconds.

Figure 2:
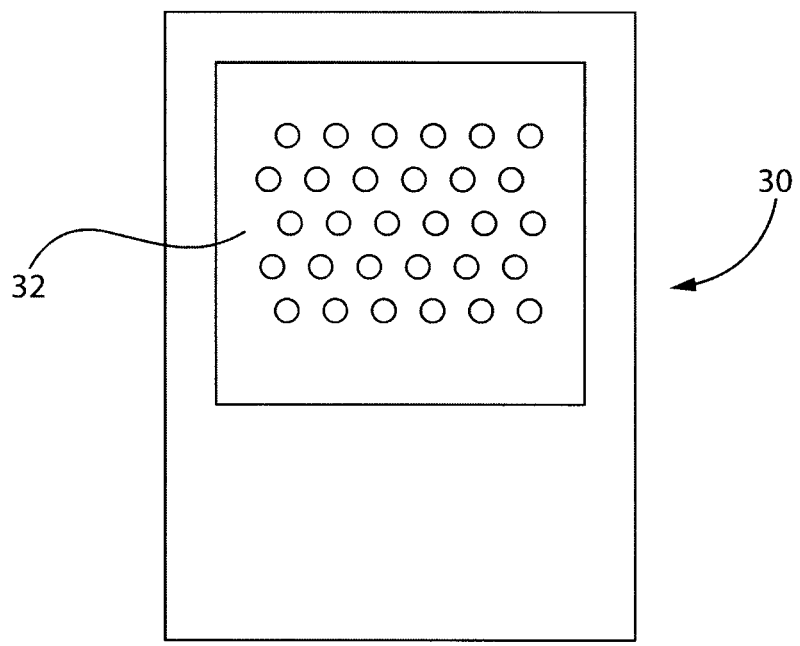
FIG. 2 shows an exemplary mask of the present invention.

Exemplary methods and apparatuses will now be described in connection with the figures. An activation system 10 is depicted in FIG. 1, including an energy source 20, a mask 30, and a roller conveyor 40 for supporting and manipulating the position/orientation of an article. As used herein, the term "mask" means a component that has the ability to either alter (e.g., limit) or substantially block the transmission of energy therethrough. The masks can have an "open area" which permits some energy transmission. The "open area" may be devoid of all material or may be a material having properties that permits energy transmission from one side of the material to the other. Masks can be made from a number of different materials and through numerous known techniques. A representative, non-limiting list includes printed nylon films, stenciled aluminum sheets/plates, silk screened quartz, and stenciled stainless still sheets/plates. Stenciling materials can be done, for example, by photochemical etching or electric discharge machining (EDM). An exemplary mask 30 with an open area design 32 is shown in FIG. 2. In one embodiment, the length L of the open area design 32 is substantially equal to the effective circumference of an article to be acted on by the present invention.

Referring again to FIG. 1, conveyor 40 contains a plurality of rollers 42 that are spaced apart so that an article can reside between adjacent rollers. Conveyor rollers 42 can rotate as they come into contact with support member 48. A substantially cylindrically-shaped article 50 is shown residing between a first roller 42a and a second roller 42b. By way of example only, article 50 can represent an applicator for inserting an intravaginal product into the body—note article 50 is depicted in a simplified manner without features typically found in such applicators. Article 50 comprises an activatable colorant, such as those described above.

Figure 3A:
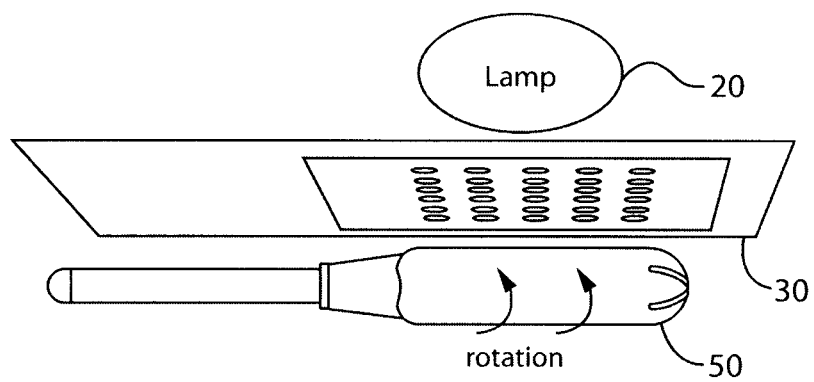
FIGS. 3A-3C depict parts of the system of FIG. 1 and an article at different positions with respect to a patterned mask, with the resulting imparted design.
Figure 3B:
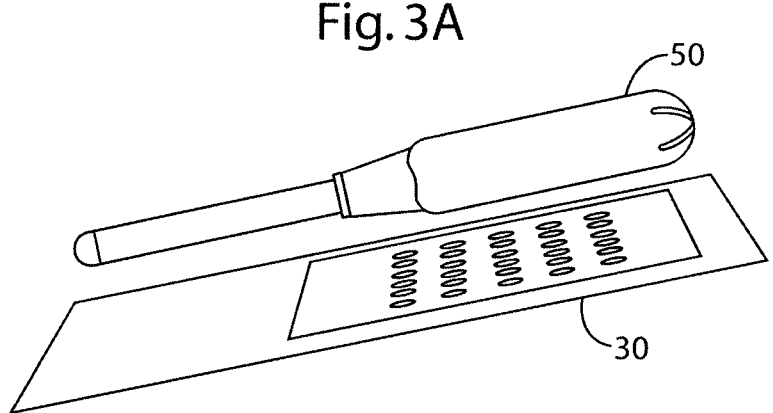
Figure 3C:
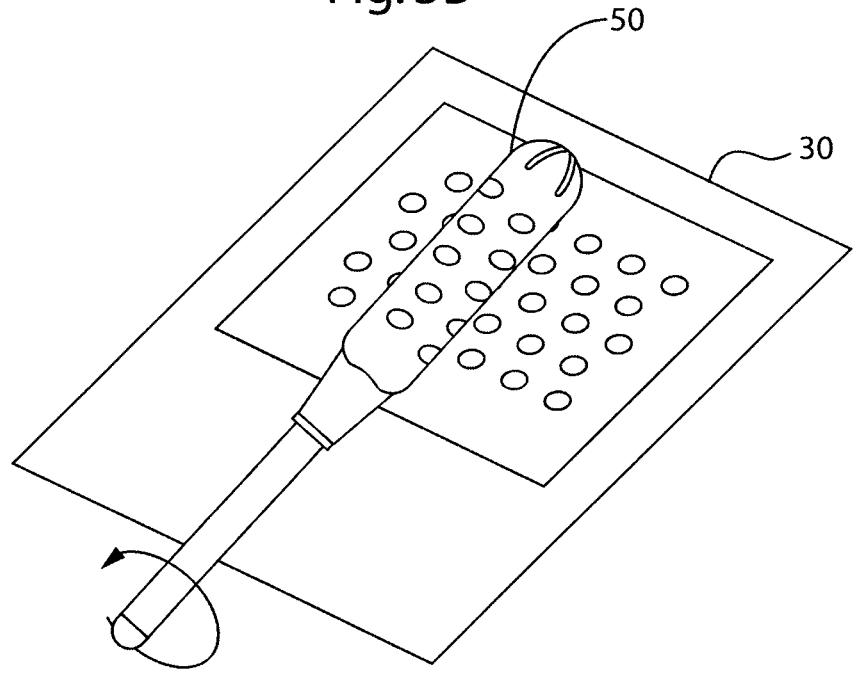

FIGS. 3A-3C show parts of the system from FIG. 1. FIG. 3A shows energy source 20, mask 30, and article 50, but does not show the system components which translate and rotated article 50. FIG. 3B shows article 50 in a first position. With reference to the components included in FIG. 1, when conveyor 40 is operated, rollers 42 are both translated and rotated. This, in turn, translates and rotates article 50 to a second position shown in FIG. 3C. Energy is directed through the open area of mask 30 while article 50 is moving from the first position to the second position. The transmitted energy activates colorant in a plurality of locations on and/or within article 50 to impart the mask open area design on and/or within the article. In one embodiment, mask 30 is held stationary while article 50 is moved and energy is being transmitted by energy source 20. It should be understood that the equipment and means of moving articles is not limited to the features shown in the figures. For example, a simple belt or flighted conveyor could be employed to support the articles, with the mask or another overlying member contacting the carried articles to cause them to rotate while receiving energy from the energy source.

Figure 4A:
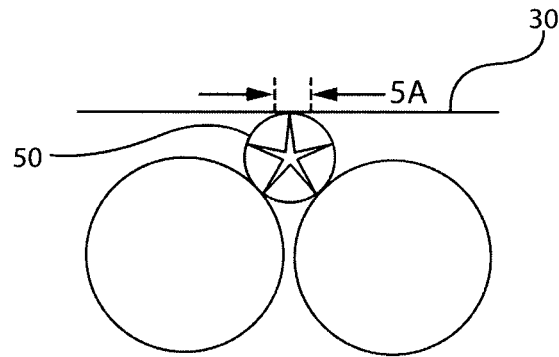
FIGS. 4A-4B illustrate embodiments that include application of a normal force to an article during processing according to the present invention.
Figure 4B:
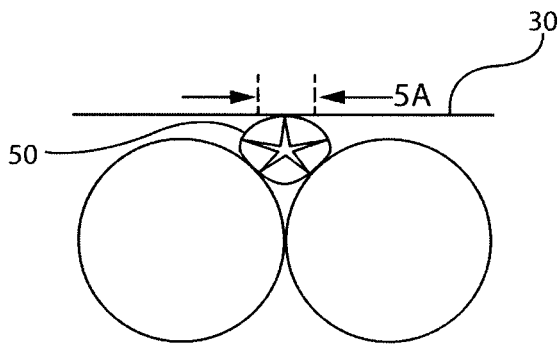

The article can be spaced apart from mask 30, or can alternatively be in contact with mask 30 to better control energy transmission and the resolution/uniformity of an imparted design. And the level of contact can range from minimal to significant. Significant contact, for example, can result in a normal that can, depending on the properties of the article, elastically deform the article so that the surface area of the article portion that is positioned perpendicular to the energy source is increased. FIG. 4A depicts the results of a relatively small applied normal force, while FIG. 4B shows an effect of a relatively greater applied normal force. Notice that the surface area SA that would be positioned perpendicular to an overlying energy source is increased with a greater applied normal force. Although a structural member (mask 30) is employed to apply a normal force to article 50 in FIGS. 4A and 4B, non-structural means, such as pressurized air, may also be employed. In should be understood that application of a normal force to increase the surface area of the article portion that is positioned perpendicular to an energy source may occur in the absence of a mask. That is, the present invention includes methods and apparatuses for activating colorants that includes application of a normal force but does not include the use of a mask or any other energy limiting device.

Figure 5:
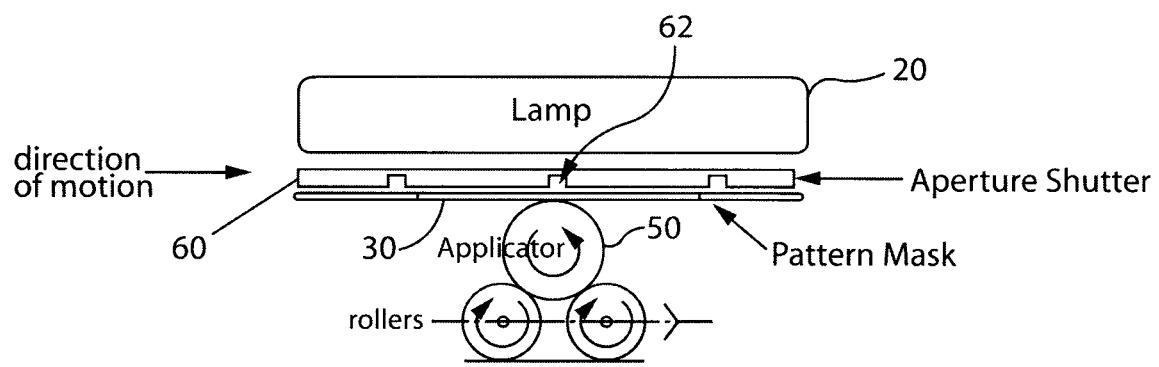
FIG. 5 is an exemplary embodiment of a system for activating colorant associated with an article, wherein the system employs an option aperture shutter conveyor.

Other techniques and components can also be employed to manage the resolution or other properties of an imparted design. For example, shutter devices can be used in conjunction with masks to control or otherwise direct energy transmission in a specified manner. An exemplary embodiment is shown in FIG. 5, wherein an aperture shutter conveyor 60 is employed between mask 30 and energy source 20. Aperture shutter conveyor 60 contains a plurality of individual apertures 62 that are selected to have a width dimension that relates to the dimension of the article portion that is substantially perpendicular to the mask and energy source. Aperture shutter conveyor 50 is preferably operated at a speed that substantially matches the translation velocity of the article as the article is passed under mask 30 and energy source 60.

Figure 6:
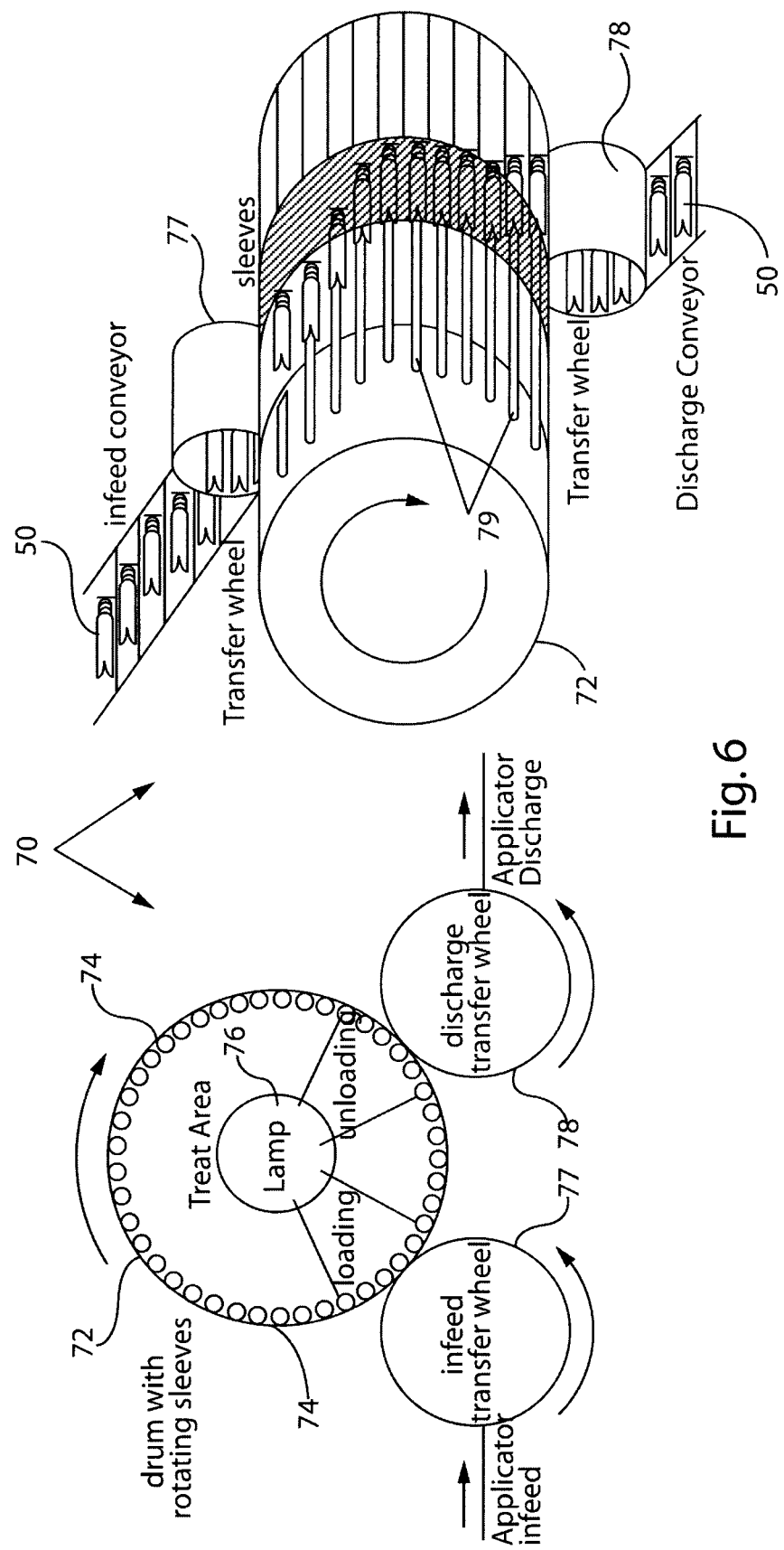
FIG. 6 depicts two views of an exemplary colorant activation system that can be used in relatively high through-put or high speed manufacturing processes.
Figure 7:
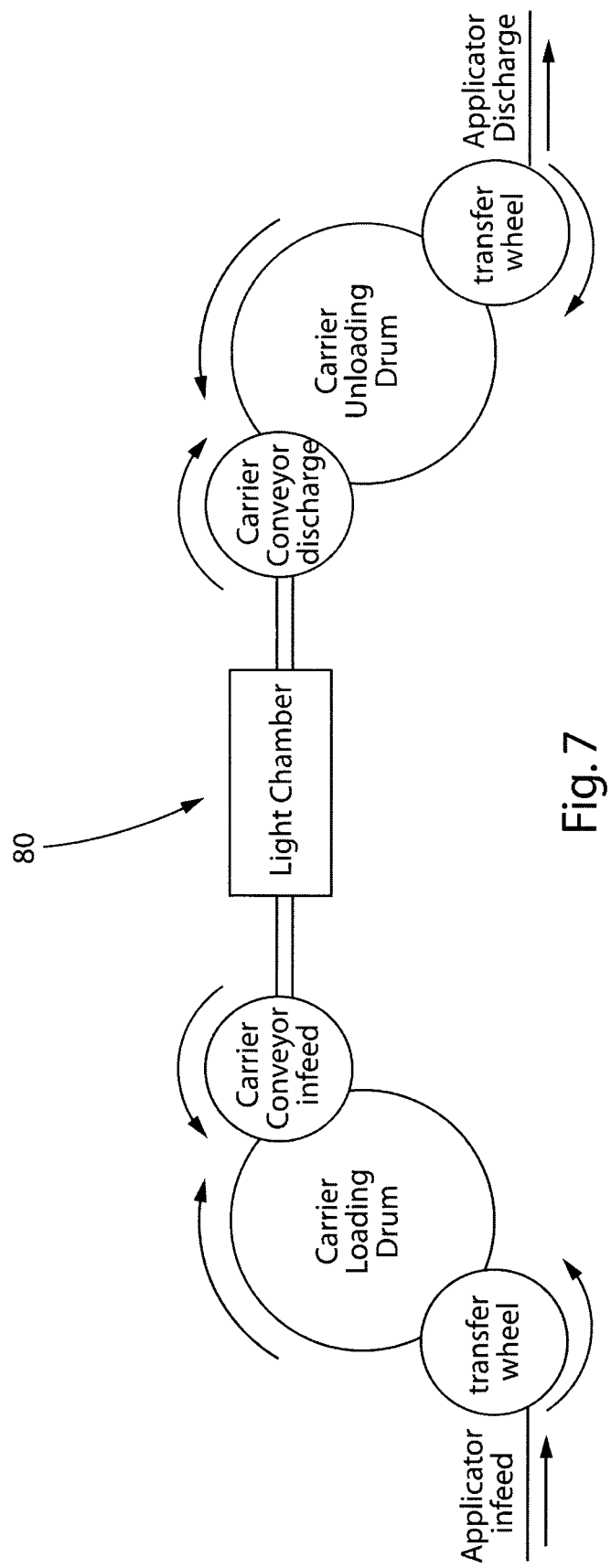
FIG. 7 shows another exemplary colorant activation system that can be used in relatively high through-put or high speed manufacturing processes.

The masks in the figures described thus far are not connected to the article and are held stationary while the article is moved in relation to the masks. In an alternative embodiment, masks can be constructed in the form of a sleeve or carrier that fits over/around the article. The sleeve can be translated and rotated in proximity to an energy source whereby activation of colorant associated with the article on various surfaces (including substantially the entire circumferential surface) can be activated. Employing a rotatable sleeve or carrier also allows for the use of rolls and drums that are conducive to high-speed processing equipment. FIG. 6 depicts two views of a first exemplary system 70 that employs a roll/drum 72 that contains a plurality of rotating sleeves 74, an energy source 76 disposed within roll 72, an article in-feed component 77, and article discharge component 78. Pushrods 79 can be used to load articles 50 into and discharge articles 50 from the individual sleeves. An alternative system 80 is depicted in FIG. 7, wherein the sleeves are not fixed to a rotating drum, but are instead coupled and decoupled using a series of rollers/drums. After a sleeve is coupled to an article, the coupled parts can be exposed to an energy source while being rotated and translated.

Figure 8:
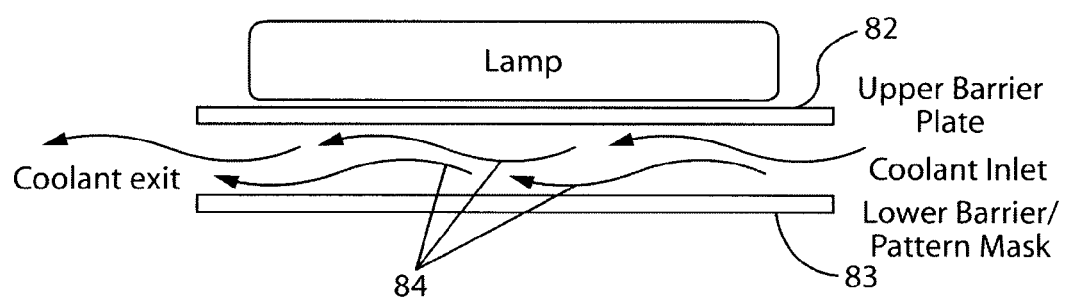
FIG. 8 depicts an exemplary cooling system that employs two spaced apart plates a coolant passing therebetween.

The figures show a single mask and a single energy source. The present invention however provides alternative configurations. In one embodiment, multiple energy sources are employed. The energy sources can be similar in type, but have different properties; e.g., a first UV lamp having a first wavelength and second UV lamp having a second wavelength. The multiple energy sources may also be two different types. Some embodiments can utilize multiple masks having similar or dissimilar open area designs and/or transmission properties. Two or more masks may be used simultaneously (e.g., at least partially overlapped) or serially. A single mask with zones of differing transmission can also be used. It should be understood that some methods of the present invention do not require a mask at all. Cooling devices may be used to help manage residual heat associated with chosen energy sources. For example, devices that continually deliver forced air, chilled air, or chilled water (or other liquids) can be placed proximate to the energy source, mask (where employed), and/or article movement components to manage heat levels. One exemplary approach, with reference to FIG. 8, is to employ a dual plate configuration having an upper pate 82, a lower plate 83 that is or comprises the previously-described mask, and coolant 84 passed between upper plate 82 and lower plate 83. Although only lower plate 83 is indicated as having a mask in FIG. 8, alternative dual plate configurations can include a mask in both of the upper and lower plates. And the masks can be similar or different from one another. The chosen coolant can vary, and can include air, water, and glycol. This configuration can help manage heat associated with the mask, particularly when the mask is held stationary and the energy source continuously or frequently transmits energy to the mask. And there is good heat transfer with this configuration since the coolant contacts the surfaces that are heating up though prolonged exposure to the energy source. A dual plate configuration can be used with or without a separate cooling device that is primary directed to the energy source itself.

The methods and apparatuses of the present invention may include additional steps and components to those described above. For example, articles can be exposed to an energy source to initially activate colorants associated with an article and then manipulated further to alter one or more visual aspects of the article created through the initial activation. Diacetylene-based colorants can change color/hue with the addition of heat after the colorants are initially activated with ultraviolet radiation. Thus, in one embodiment, an article comprising activatable colorant can be exposed to electromagnetic radiation whereby a design is created on/within a first portion of the article. The article is then heated so that the visual appearance of the first portion changes and/or the visual appearance of a second portion of the article changes.

Figure 9:
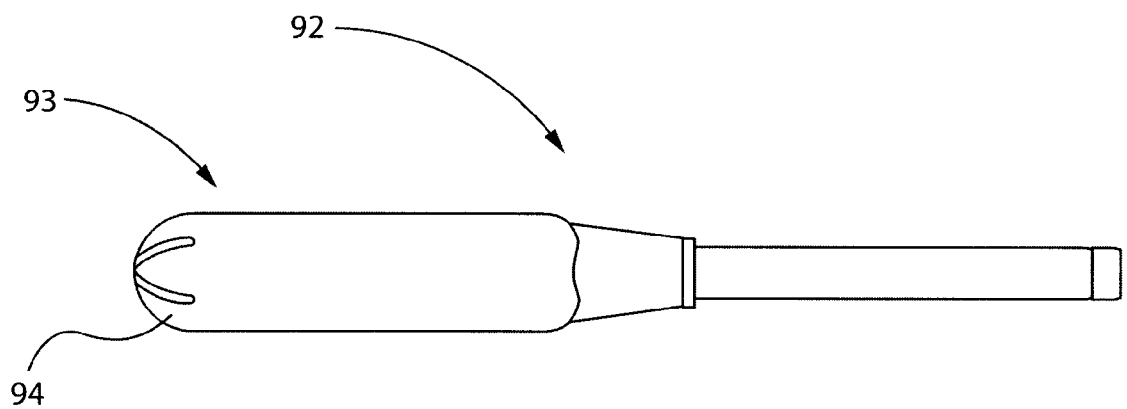
FIG. 9 shows a tampon applicator, which is one article that can be processed according to the systems and methods of the present invention.

Articles that are used for holding and/or delivering a product can include a closable end that is closed after a product is loaded within the article and opened to subsequently retrieve or deliver the contained product. Applicators for inserting a feminine hygiene product (e.g., tampon, incontinence device) are an example of such an article. With reference to FIG. 9, a tampon applicator 92 is shown having a plurality of petals 94 on its applicator insertion end 93. As shown in FIG. 9, petals 94 are converged towards one another to form a closed insertion end to facilitate a more comfortable insertion into the body. Petals 94 can then flex outwardly to allow the contained tampon to be expelled from applicator 92 and placed into the vaginal canal. Applicator 92 has a narrowed finger grip portion that requires loading the tampon via insertion end 93. Thus when applicator 92 is formed (e.g., via injection molding), petals 94 are formed in an "open position" and require a molding or other step after the tampon is placed into the applicator. And this typically involves heat and pressure. Molding the petals into a closed position via heat and pressure can occur before or after a step of activating colorant associated with the tampon applicator. If done after the colorant activation, the petal molding may alter the color of the petal region of the applicator and/or other regions of the applicator including the region visually altered via the activation process. If the petals are molded in a closed position before the colorant activation step, then the molding process will unlikely affect the color of the applicator since the colorant has not yet been activated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for activating colorant associated with an article, the method comprising the steps of:
    a. providing an energy source;
    b. providing an article comprising an activatable colorant;
    c. disposing a mask between the energy source and the article, the mask comprising an open area design;
    d. directing energy through the open area of the mask and onto/into the article; and
    e. moving the article from a first position to a second position that is different from the first position while conducting step (d) so that the activatable colorant in a plurality of locations on/in the article is activated whereby the open area design is substantially created on and/or within a portion of the article, wherein the mask is stationary while conducting step (e), wherein the article is both rotated and translated during step (e), and wherein a portion of the article is elastically deformed during step (e).

2. The method of claim 1, wherein the length of the open area design is substantially equal to a circumference of the article.

3. The method of claim 1, wherein step (e) is conducted with a roller conveyor comprising a first roller and a second roller.

4. The method of claim 1, wherein the article is in contact with the mask.

5. The method of claim 1, wherein the article comprises at least one of a thermoplastic polymer and a thermoset polymer.

6. The method of claim 1, wherein the article comprises fiber.

7. The method of claim 1, wherein the article is an injection molded article.

8. The method of claim 1, wherein the article is a blow molded article.

9. The method of claim 1, wherein the article is an applicator for a feminine hygiene product.

10. The method of claim 1, wherein the article is a container.

11. The method of claim 1, wherein the article is a toothbrush handle.

12. The method of claim 1, wherein the energy source comprises an ultraviolet light source.

13. The method of claim 1, wherein the energy is electromagnetic radiation.

14. The method of claim 1, wherein the activatable colorant comprises a diacetylene-based compound.

15. A method for activating colorant associated with an article, the method comprising the steps of:
    a. providing an energy source;
    b. providing an article comprising an activatable colorant;
    c. disposing a mask between the energy source and the article, the mask comprising an open area design;
    d. directing energy through the open area of the mask and onto/into the article; and
    e. moving the article from a first position to a second position that is different from the first position while conducting step (d) so that the activatable colorant in a plurality of locations on/in the article is activated whereby the open area design is substantially created on and/or within a portion of the article, wherein a portion of the article is elastically deformed during step (e).

16. The method of claim 15, wherein the article is in contact with the mask during step (e).

* * * * *